United States Patent
Koley et al.

(10) Patent No.: US 8,252,598 B2
(45) Date of Patent: Aug. 28, 2012

(54) METHOD OF SENSING CHEMICAL AND BIO-MOLECULAR ANALYTES AND SENSING SYSTEM USING A MICROCANTILEVER

(75) Inventors: Goutam Koley, Columbia, SC (US); Muhammad Qazi, Columbia, SC (US); Thomas Vogt, Chapin, SC (US); Sangmoon Park, Busan (KR)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 12/442,954

(22) PCT Filed: Nov. 27, 2007

(86) PCT No.: PCT/US2007/085615
§ 371 (c)(1),
(2), (4) Date: Mar. 4, 2010

(87) PCT Pub. No.: WO2008/067298
PCT Pub. Date: Jun. 5, 2008

(65) Prior Publication Data
US 2010/0173422 A1 Jul. 8, 2010

Related U.S. Application Data

(60) Provisional application No. 60/861,226, filed on Nov. 27, 2006, provisional application No. 60/921,419, filed on Apr. 2, 2007, provisional application No. 60/922,051, filed on Apr. 5, 2007.

(51) Int. Cl.
*G01N 27/00* (2006.01)
*G01N 27/04* (2006.01)
*H04R 17/00* (2006.01)
*H05K 13/00* (2006.01)

(52) U.S. Cl. ......... 436/149; 436/63; 436/86; 422/82.02; 422/88; 73/24.01; 73/24.06; 435/287.2

(58) Field of Classification Search .................. 436/149, 436/63, 86; 73/24.01, 24.06; 435/6, 287.2; 422/88, 82.01
See application file for complete search history.

(56) References Cited

U.S. PATENT DOCUMENTS 4,605,626 A * 8/1986 Beck .................. 204/403.06
5,494,831 A    2/1996 Kindler
6,823,717 B2  11/2004 Porter et al.
(Continued)

OTHER PUBLICATIONS

Baller et al., A cantilever array-based artificial nose, *Ultramicroscopy*, 82, 1, (2000).

(Continued)

*Primary Examiner* — Christine T Mui
(74) *Attorney, Agent, or Firm* — Dority & Manning, P.A.

(57) ABSTRACT

Methods and systems of detecting analytes using a microcantilever system are generally described. The microcantilever system generally includes micro- or nano-sized elements that can be electrostatically driven to resonance. Utilizing the disclosed devices and methods, direct electronic detection of the resonant frequency, changes of the resonant frequency, and associated phase signal of a micro- or nano-sized element can be utilized to measure the presence of a targeted analyte. The detection system of the present invention utilizes a non-contact microcantilever device. That is, the surface of the microcantilever (e.g., the surface of the resonating beam) does not bond or otherwise attach to an analyte or other chemical. Thus, the microcantilever device, including the resonating beam, can be kept in pristine condition during and even after repeated use.

20 Claims, 10 Drawing Sheets

U.S. PATENT DOCUMENTS

| | | | |
|---|---|---|---|
| 7,105,301 B2 | 9/2006 | Su et al. | |
| 2004/0115711 A1* | 6/2004 | Su et al. | 435/6 |
| 2004/0194534 A1* | 10/2004 | Porter et al. | 73/24.01 |
| 2006/0255790 A1* | 11/2006 | Gaillard et al. | 324/76.41 |

OTHER PUBLICATIONS

Battiston, et al., "A chemical sensor based on a microfabricated cantilever array with simultaneous resonance-frequency and bending readout", *Sens. and Act., B-Chemical*, 77, 122, (2001).

Blain, et al., "Towards the hand-held mass spectrometer: design considerations, simulation, and fabrication of micrometer-scaled cylindrical ion traps", *International J. of Mass Spectrometry*, 236, 91, (2004).

Butikov, et al., "Parametric excitation of a linear oscillator", European Journal of Physics, 25, 535, (2004).

Bourgeois, et al., "The use of sensor arrays for environmental monitoring: interests and limitations", *J. Environ. Monitoring*, 5, 852, (2003).

Carrascosa, et al., "Nanomechanical biosensors: a new sensing tool", *Trac-TrendsAnal. Chem.*, 25, 196, (2006).

Cotte-Rodriguez, et al., "Non-proximate detection of explosives and chemical warfare agent simulants by desorption electrospray ionization mass spectrometer", *Chem. Comm.*, 28, 2968 (2006).

Cui, et al., "Nanowire nanosensors for Highly-Sensitive, and Selective Detection of Biological and Chemical Species", *Science*, 293, 1289, (2001).

Dickinson, et al., "Current trends in "artificial-nose" technology", *Trends in Biotechnology*, 16, 250, (1998).

Feng, et al, "Progress in ion mobility spectrometry", *Progress in Chrmistry*, 17, 514 (2005).

Greene, et al., "Calorimetric molecularly imprinted polymer sensor array using dye displacement", J. Amer. Chem. Soc., 127, 5695, (2005).

Greene, et al., "Molecularly imprinted polymer sensor arrays", Chem. Comm., 10, 1172, (2004).

Hines, et al., "Electronic noses: a review of signal processing techniques", *IEEE Proceedings—Circuits Devices and Systems*, 146, 297, (1999).

Hansen, et al., "Microcantilever Biosensor", *Methods*, 37, 57, (2005).

Huang, et al., "Nanomechanical hydrogen sensing", Appl. Phys. Lett., 86, 143104, (2005).

Hwang et al., "Carrier Transport in Two-dimensional Graphene Layers", Phys. Rev. Lett. 98, 186806, (2007).

Ilic, et al., "Attogram detection using nanoelectromechanical oscillators", *J. Appl. Phys.* 95, 3694, (2004).

Koley, et al., "nanoscale capacitance-voltage characterization of two-dimensional electron gas in AlGaN/GaN heterostructures", Jap. J. Appl. Phys. Lett., 44, L1348, (2005).

Koley, et al., "Gas Sensing using Electrostatic Force Potentiometry", Appl. Phys. Lett., 90, 173105 (2007).

Koley, et al, "Surface potential measurements on GaN and AlGaN/GaN heterostructures by scanning Kelvin probe microscopy", *J. Appl. Phys.* 90, 337, (2001).

Lavrik, et al., "Femtogram mass detection using photothermally actuated nanomechanical resonators", *Appl. Phys. Lett.* 82, 2697, (2003).

Lavrik, et al., "Cantilever transducers as a platform for chemical and biological sensors", *Rev. Sci. Instrum.*, 75, 2229, (2004).

Levin, et al., "Fourier transform infrared vibrational spectroscopic imaging: Integrating microscopy and molecular recognition," *Ann. Rec. of Phys. Chem.*, 56, 429 (2005).

Miller et al., "A MEMS radio-frequency ion mobility spectrometer for chemical vapor detection", *Sensors and Actuators A Physical*, 91, 301, (2001).

Mukhopadhvav, et al., "Nanomechanical sensing of DNA sequences using piezoresistive cantilevers", *Langmuir*, 21, 8400, (2005).

Novak, et al., "Nerve agent detection using networks of single-walled carbon nanotubes", Appl. Phys. Lett., 83, 4026, (2003).

Novoselov, et al., "Electric field effect in atomically thin carbon films", *Science*, 306, 666, (2004).

Park, et al., "The preparation and characterization of photocatalytically active TiO2 thin films and nanoparticles using Successive-Ionic Layer-Adsorption- and -Reaction", *Thin Solid Films*, 15, 1250, (2007).

Pinnaduwage, et al., "Detection of trinitrotoluene via deflagration on a nnicrocantilever", *J. Appl. Phys.*, 95, 5871, (2004).

Qazi, et al., "NO2 detection by adsorption induced work function changes in In2O3 thin films", *Appl. Phys. Lett.*, vol. 91, Issue 4, 2007.

Rand, et al., "Lecture Notes on Nonlinear Vibrations", Version 52, (2005).

Schedin, et al, "Detection of individual gas molecules by graphene sensors", presented at the APS Conference, Denver, CO, (2007).

Snow, et al., "Chemical Detection with a Single-walled Carbon Nanotube Capacitor", *Science*, 307, 1942, (2005).

Staples, et al., "Ultrahigh-speed chromatography and virtual chemical sensors for detecting explosives and chemical warfare agents", *IEEE Sensors Journal*, 5, 622 (2005).

Thundat, et al., "Vapo Detection Using Resonating Microcantilevers", Anal. Chem. 67, 519, 1995.

Toal et al., "Polymer Sensors for nitroaromatic explosives detection", J. Mater./ Chem., 16, 2871, (2006).

Tsai, et al., On the Hydrogen Sensing Properties of a Pt-Oxide-$In_{0.5}Al_{0.5}P$ Schottky Diode, 2006.

Turner, et al., Five parametric resonances in a microelectromechanical system, *Nature*, 396, 149, (1998).

Valentini, et al., "Sensors for sub-ppm $NO_2$ down to ppb levels using individual and multiple $In_2O_3$ nanowire devices", *Nano Lett.*, 4, 1919, (2004).

Valentini, et al., "Interaction of methane with carbon nanotube thin films: role of defects and oxygen absorption", *Materials Science & Engineering C-Biomimetic and Supramolecular Systems*, 24, 527, (2004).

Wu, et al., "Bioassay of prostate-specific antigen (PSA using microcantilevers", *Nature Biotechnology*, 19, 856, (2001).

Zhang, et al., "Application of parametric resonance amplification in a single-crystal silicon micro-oscillator based mass sensor", Sens. and Act. A—Physical, 122, 23, (2005).

Zhang, et al., "Detection of NO2 down to ppb Levels Using Individual and Multiple In2O3 Nanowire Devices" *NanoLetters*, 2004, vol. 4, No. 10, pp. 1919-1924.

International Search Report for WO 2008/067298.

\* cited by examiner

METHOD OF SENSING CHEMICAL AND BIO-MOLECULAR ANALYTES AND SENSING SYSTEM USING A MICROCANTILEVER

RELATED APPLICATIONS

The present application claims priority to the following U.S. Provisional Patent Applications: (1) Ser. No. 60/861,226 filed on Nov. 27, 2006 titled "Novel Method of Developing Chemical and Bio-molecular Sensors Using a Coated Microcantilever System", (2) Ser. No. 60/921,419 filed on Apr. 2, 2007 titled "Novel Sensor using Microcantilever System", and (3) Ser. No. 60/922,051 filed on Apr. 5, 2007 titled "Novel Sensor using Microcantilever System", all of which are incorporated herein by reference.

GOVERNMENT SUPPORT CLAUSE

The present invention was developed with funding from National Science Foundation Grant 0630097. The government retains certain rights in the invention.

BACKGROUND OF THE INVENTION

Micro-electromechanical systems (MEMS) have been extensively used as sensors for a variety of mechanical parameters such as pressure, flow, mass, and stress. In addition, they have been used for several electrical applications, such as filters and switches in Integrated Circuits and high quality factor (high-Q) oscillators. Micro-electromechanical systems (MEMS) and more recently nano-electromechanical systems (NEMS) have also been widely studied for the detection of chemicals and bio-molecules. Chemical sensors have widespread industrial and environmental applications including toxic gas sensing, process flow monitoring, and pollution control. Bio-molecule sensors on the other hand are extremely useful for label-free detection in lab-on-a-chip type applications, bio-hazard detection for counter-terrorism, and homeland security.

The microcantilever used in a scanning probe microscope (SPM) in non-contact or tapping modes is essentially a MEMS device. The advantage of using a microcantilever in measurements such as in a SPM, include high quality factors of such oscillatory systems, easy batch fabrication using standard lithographic techniques, and a base material (commonly Si) with tunable electrical properties. In recent years, there has been a large focus on using the micro(nano)cantilevers as sensor elements for specific chemical and biological species. These applications exploit the above mentioned advantages associated with micro(nano)cantilevers, in addition to the requirements of low power and very small sample quantity for detection.

In a MEMS/NEMS detection system, an electrical signal is converted to mechanical oscillations of a resonator, which under the influence of external agents (analyte molecules), changes its resonance characteristics. This change is then converted back into an electrical signal enabling detection. MEMS based sensing is usually preferred due to its extremely high sensitivity resulting from its very high quality factor (in the range of $10^5$-$10^7$ in vacuum), which greatly exceeds that of its electrical counterparts. In addition, the power consumed by these sensors is very low, so a large array of these sensors can be packed together with very low power dissipation, for lab-on-a-chip or multi-functional sensing applications. There are two basic mechanisms by which the MEMS based devices commonly sense analyte molecules: (i) change in resonance curve due to a change in mass attached to the cantilever or beam resonator, and (ii) change in resonance curve due to the stress induced in the cantilever or beam by the attached molecules.

In the past, one of the most common techniques to detect specific types of molecules (usually larger bio-molecules) is to detect the change in resonance frequency of very high-Q cantilevers due to specific molecular attachment (causing changes in mass). The specificity is obtained through functionalization of the cantilever surface using a specific coating that enables the attachment of target molecules. Using micro (nano)cantilever resonators in high vacuum conditions, mass detection down to sub-attogram level has been demonstrated. Another very commonly used detection methodology involves using a chemical field effect transistor (Chem-FET), which is basically a gateless FET whose surface is functionalized with appropriate coating for specific molecular attachment. In such a device, the surface barrier potential changes due to attachment of the target molecules. Since the barrier potential change is related to the current, the latter can be measured to detect the attachment of the target molecules. In these past detection systems, the external agents (analyte molecules) attach themselves directly to the functionalized surface of the microcantilever. Thus, after exposing the microcantilever to an environment to be tested, the surface of the microcantilever must be cleaned (i.e., remove any attached analytes from the surface) or replaced. Presently, it is more economical to simply replace the microcantilever after each use. However, replacing the microcantilever after each use increases the cost dramatically, not to mention being wasteful.

As such, a need exists to allow for a method and system that employs a reusable microcantilever for the detection of analytes.

SUMMARY OF THE INVENTION

Objects and advantages of the invention will be set forth in part in the following description, or may be obvious from the description, or may be learned through practice of the invention.

In general, the present invention is directed to development of novel chemical and bio-molecular sensors based on a reusable microcantilever system. For example, the system can include a microcantilever device having a resonating element positioned within working proximity of a counter electrode. The counter electrode includes a sensing surface (e.g., graphite or a nanostructure) configured to bond to an analyte. The detection device is configured to monitor the movement of the resonating element. In one embodiment, the microcantilever device can be positioned within a vacuum.

Additionally, in one embodiment, the sensing surface can include a plurality of different functionalized electrodes. For example, the microcantilever can be configured to move across the sensing surface in a plane that is parallel with the sensing surface such that the microcantilever can be positioned in working proximity to each of the differently functionalized electrodes.

In another embodiment, the present invention is directed to a method of forming a detection system for detecting the presence of an analyte. A microcantilever device comprising a resonating element is positioned within working proximity of a sensing surface on a counter electrode. A detection device configured to monitor the movement of the resonating element.

In yet another embodiment, the present invention is directed to a method of detecting the presence of an analyte. The method includes providing a detection system having a microcantilever device positioned within working proximity to a counter electrode. The microcantilever device comprises a resonating element, and the counter electrode comprises a sensing surface configured to bond to an analyte. The change in surface work function or charge configurations of the sensing surface is measured or detected utilizing a detection device configured to monitor the movement of the resonating element.

Other features and aspects of the present invention are discussed in greater detail below.

BRIEF DESCRIPTION OF THE FIGURES

A full and enabling disclosure of the present invention, including the best mode thereof to one skilled in the art, is set forth more particularly in the remainder of the specification, which includes reference to the accompanying figures, in which.

Repeat use of reference characters in the present specification and drawings is intended to represent the same or analogous features or elements of the present invention.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

In general, the present disclosure is directed to methods of detecting analytes using a microcantilever system. The microcantilever system generally includes micro- or nano-sized elements that can be electrostatically driven to resonance. More specifically, utilizing the disclosed devices and methods, direct electronic detection of the resonant frequency, changes of the resonant frequency, and associated phase signal of a micro- or nano-sized element can be utilized to measure the presence of a targeted analyte.

The presently disclosed methods and systems can facilitate the formation of economical, portable NEMS and MEMS devices suitable for use in practical, real-world applications. The disclosed methods can be utilized with other devices as well, for instance, the disclosed methods can be utilized in development of high quality electronic filters as well as other high quality (high Q factor) electronic devices. Additionally, the microcantilever system includes a microcantilever that can be reused a plurality of times.

The detection system and methods of the present invention generally include a microcantilever device positioned in working proximity to a sensing surface. By keeping the sensing surface separate from the microcantilever, the system can be reused simply by replacing or cleaning the separate sensing surface without the need for a new microcantilever device. Additionally, the sensing surface can be replaced (so as to refresh or to detect a different targeted analyte) without having to disturb the microcantilever device.

Specifically, the detection system of the present invention can utilize a non-contact microcantilever device. That is, the surface of the microcantilever (e.g., the surface of the resonating beam) does not bond or otherwise attach to an analyte or other chemical. Thus, the microcantilever device, including the resonating beam, can be kept in pristine condition during and even after repeated use. Additionally, through the use of a non-contact microcantilever device, there is no need to functionalize the surface of the resonating beam in a particular manner depending on the targeted analyte. Thus, there can be more uniformity in the manufacture of each microcantilever device.

Figure 1:
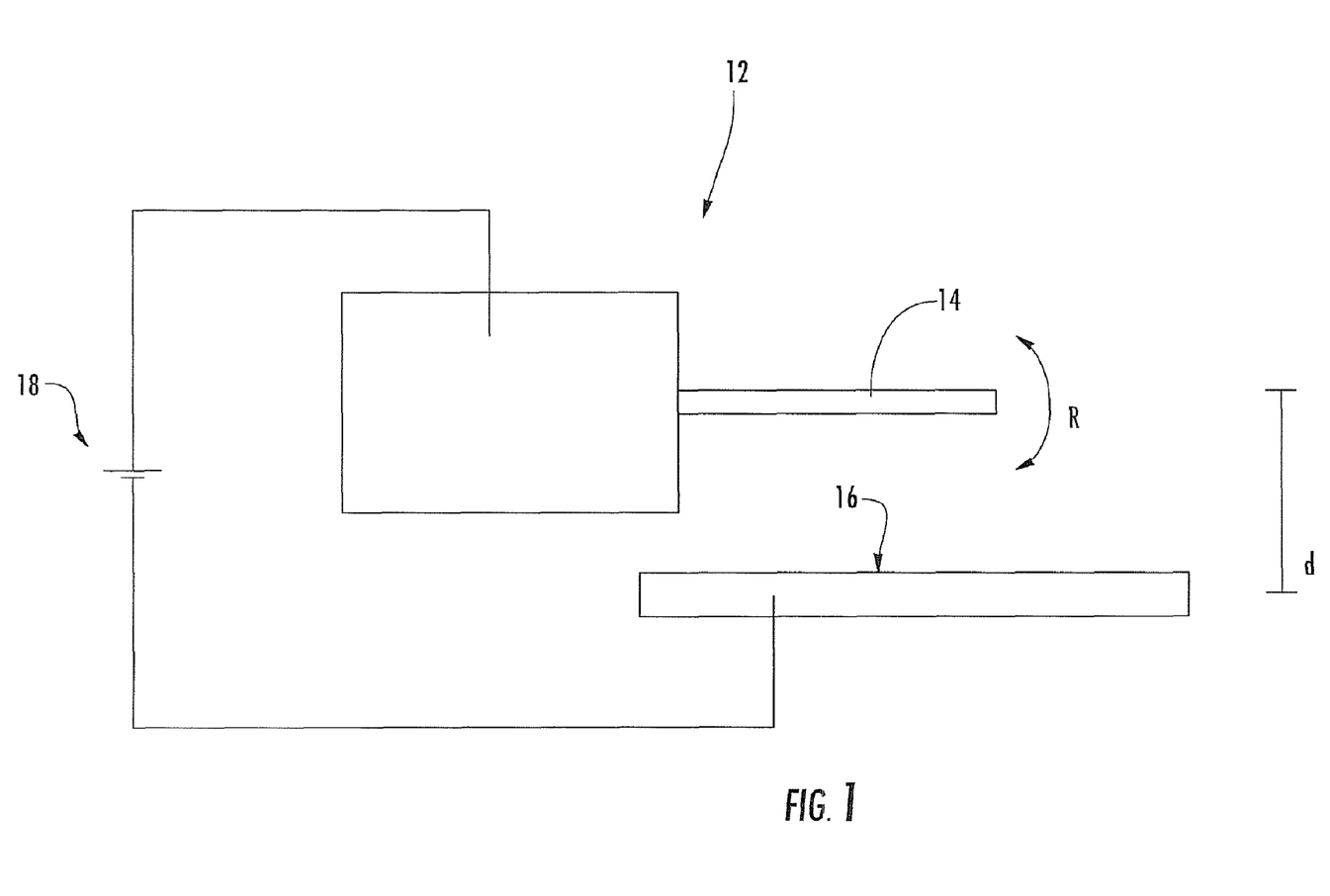
FIG. 1 shows a prospective view of an exemplary detection system of the present invention.

Referring to FIG. 1, a detection system 10 is shown having a microcantilever device 12 with a resonating 14 and a sensing surface 16. Although shown as a resonating beam 14 having a rectangular shape, it should be understood that any other shaped resonating element can be utilized in accordance with the present invention. Both the microcantilever device 12 and the sensing surface 16 will be discussed in greater detail below.

As shown, the resonating beam 14 is positioned within working proximity (measured by the distance d) to the sensing surface 16, so as to induce a charge on the resonating beam 14 while remaining in a non-contact mode. The preferred gap distance between the sensing surface 16 and the resonating beam 14 can vary, and can depend, for instance, upon the nature of the atmosphere surrounding the system and on the geometric relationship between the microcantilever device 12 and the sensing surface 16. In general, however, the intervening distance between the resonating beam 14 and the sensing surface 16 can be at least enough so as to ensure no contact between the sensing surface 16 and the resonating beam 14 at resonance, while ensuring the capability of establishing a capacitance driven electrostatic force on the microcantilever device 12.

A voltage is applied to the detection system 10, so as to induce a modulated electrostatic force on the cantilever. The detection system 10 can also include a signal generator 18, shown as an ac voltage generator. The voltage applied to the sensing surface 16 can induce an electrostatic force on the resonating beam 14, which, at the appropriate parameters, can force the resonating beam 14 into resonance.

Figure 2:
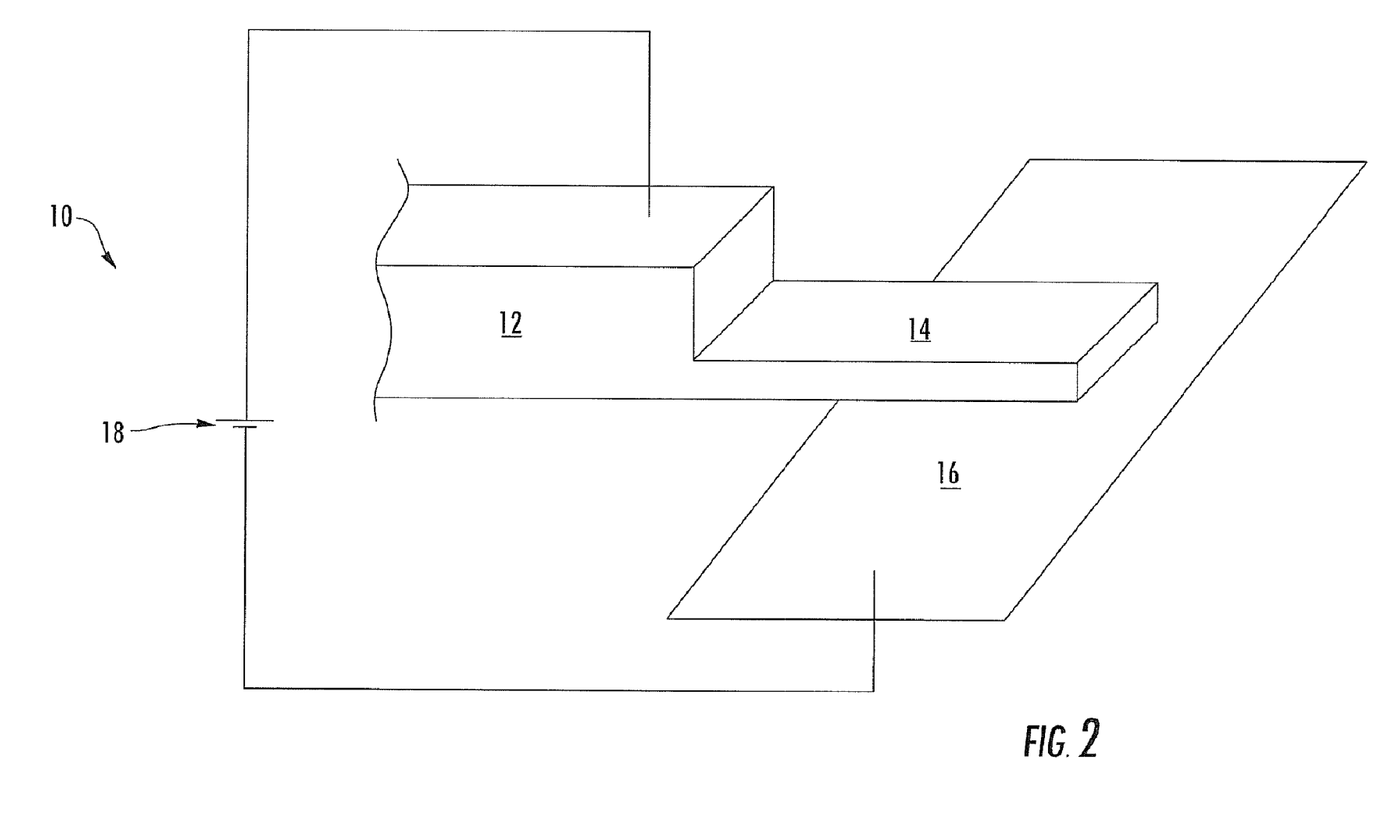
FIG. 2 depicts a side view of the exemplary detection system of FIG. 1.

In FIGS. 1 and 2, the resonating beam 14 is positioned above the sensing surface 16 such that the resonating beam 14 and the sensing surface 16 are substantially parallel to each other. However, any other configuration (e.g., tip-to-tip) could be utilized in accordance with the present invention.

I. Microcantilever Device

The microcantilever device 12 can include one or more micro-sized or nano-sized elements. For example, the devices can utilize one or more micro-sized beams, such as the resonating beam 14 shown in FIGS. 1-2. In general, micro-sized beams can be classified as those having micrometer dimensions, e.g., greater than about 1 micrometer ($\mu m$) in width and/or thickness. For example, micro-cantilevers of the present invention can have a length dimension less than about 500 $\mu m$, for instance between about 90 $\mu m$ and about 350 $\mu m$ and a width dimension less than about 50 $\mu m$, for instance between about 10 $\mu m$ and about 50 $\mu m$. Nano-sized beams generally include those elements having width and/or thickness dimensions less than the micro-sized devices (e.g., less than about 1 $\mu m$). For instance, in one embodiment, nano-sized elements of the invention can have a width and/or thickness dimension less than about 500 nm. Nano-sized elements can, however, have a length in the micrometer range. For instance, one exemplary nano-cantilever of the invention can have a generally circular cross-section of between about 1 nm and about 200 nm in diameter, and a length in the micrometer range, for instance greater than about 5 $\mu m$.

The beams of the devices can have any geometric shape and can have an aspect ratio (L/D) greater than about two. Moreover, though much of the following discussion is directed to embodiments in which the beams are provided in a device as a cantilever, i.e., clamped at a first end and free to vibrate at a second end, the presently disclosed methods and devices are equally applicable to a beam provided in other orientations. For example, the invention is also directed to devices in which the disclosed beam is clamped at both ends, i.e., a double-clamped beam. In particular, the presently disclosed invention encompasses any micro- or nano-sized element that can be electrostatically driven into resonance.

The elements of the disclosed devices can generally be formed of any material including a suitable conductive or semi-conductive material at least at the surface of the element. For instance, in one embodiment, an element can be formed of a non-conductive base substrate that has been coated with a conductive outer layer. Fabrication materials and techniques for forming many structures suitable for use in the presently disclosed devices are generally known to those of ordinary skill in the art. For example, materials encompassed by the invention include metallic nanowires, gallium arsenide/aluminum arsenide structures, nanocrystalline diamond films, and materials based upon silicon including, but not limited to, silicon on insulator structures, silicon carbide on silicon structures, aluminum nitride on silicon structures, and amorphous silicon nitride structures.

In one embodiment, the elements of the disclosed devices can be nanostructures, and in one particular embodiment, carbon-based nanostructures. For example, carbon-based nano-cantilevers of the disclosed devices can be formed from nanotubes, including single-walled nanotubes (SWNT) and multi-walled nanotubes (MWNT), nanobelts, nanorods, nanowires, nanocoils, and the like. In addition, the elements can be formed of more than one nanostructure in combination, for example, a bundle of nanotubes, or a stack of nanobelts, or even combinations of two or more structures of different shapes. Nanostructures of the invention are not limited to carbon-based nanostructures, however, and nanostructures formed of other material can be utilized. For example, nanostructures etched from silicon or including any other suitable conductive or semi-conductive material at the surface can be utilized. In this respect, other resonating structures, such as beams attached at both ends can also be used for the non-contact detection.

In general, the elements of the disclosed devices can be formed according to any known formation method and of any suitable material. For example, carbon-based nano-cantilevers of the invention can be formed via physical evaporation methods such as vapor-liquid-solid (VLS) processes, chemical vapor deposition (CVD) methods, catalyst assisted processes, processes involving electric arc gas discharge, pulsed laser ablation techniques, or by simple mechanical abrasion, as are generally known to those of ordinary skill in the art.

In one particular embodiment, the microcantilever device can be positioned in a vacuum. By positioning the microcantilever device in a vacuum, any potential contact between the microcantilever and any environmental contaminants are avoided. Thus, false readings can be minimized. In addition, the quality factor of the resonance increases dramatically in vacuum (usually 100-1000 times) causing exceptional sensitivity toward molecules that can absorb on the functionalized surface outside of the vacuum enclosure.

II. Sensing Surface

The sensing surface can be constructed of any suitable material that has an affinity for the targeted analyte. One of ordinary skill in the art would be able to functionalize the sensing surface to attract and bond (e.g., covalent bond, ionic bond, hydrogen bond, etc.) to the targeted analyte(s).

Also, the sensing surface acts as a counter electrode to the microcantilever to complete the detection system circuit. Although the sensing surface itself may have only marginal conductivity, the sensing surface can be located on a more conductive material, such as a metal electrode or a semiconductor attached to an electrode. In one particular embodiment, the sensing surface can be applied on semiconductor substrate.

For example, when sensing nitrogen oxides, the sensing surface can be silicon or silicone oxide. Gases such as NOx (where x is 1 or 2), $NH_3$, and $H_2S$ have the property of releasing or accepting electrons when in contact with transition metal oxides, such as $In_2O_3$, $SnO_2$ and ZnO. In this embodiment, the reference electrodes (i.e. the counter electrode) can be coated with these materials, and the surface potential changes can be measured at room temperature and/or at elevated temperatures.

In another embodiment, the present inventors have discovered that the use of thin graphite films is suitable for sensing the above-mentioned gases. Thin films of graphite can be produced economically on a variety of substrates, including metals, semiconductors and insulators. As used herein, the term "graphite" is meant to encompass graphite in any form. In one particular embodiment, nanostructured graphite (NG) can be used as the functionalization layer, which can be deposited easily and inexpensively on a variety of substrates by simple mechanical abrasion on the substrate or by coating powders (comprising nanoscale particles) of graphite. The NG layer can mostly include of crystalline graphene films with nanoscale dimensions, creating a large surface area. This enormous surface area of the NG films leads to very high sensitivity, possibly much higher than continuous and fully crystalline graphene layers. The dimensions of the graphene sheets used in the functionalization layers can be controlled to enhance sensitivity. Graphene films, which consist of a single layer of carbon atoms are sensitive to a variety of molecules. For electron poor gases such as $NO_2$, detection down to a single molecular level is possible. Graphene is a unique material that is truly two-dimensional, and has electron and hole mobilities of several thousands at room temperature with carrier concentration reaching as high as mid $10^{13}$ cm$^{-2}$. A remarkable property of graphene is that it is ambipolar (both electrons and holes carry current simultaneously), with a slight overlap of a few tens of meV between the conduction and valence band edges. Therefore, it is relatively easy to make a few layer graphene (FLG) film p-type or n-type (holes or electrons as the net carriers) by applying appropriate bias between the graphene film and a metal electrode separated by an insulator (such as $SiO_2$). The bias dependent polarity of graphene presents a unique opportunity for sensing applications, since the adsorption of electron-rich and electron-poor molecules on a material surface is significantly influenced by porn-type nature of the material.

The graphene sensing surface can be made by coating graphene layer onto a grounded substrate. The process used to create these films in this case is not (1) the more commonly used physical deposition using sputtering or pulsed laser deposition or even (2) the economically attractive chemical deposition technique, which lends itself to commercialization. The process used to create these films involves applying graphite (such as from a readily available pencil) onto a substrate such as metal or even paper. Of course, any method of applying graphite to form the sensing surface can be utilized.

In other embodiments, the sensing surface can include nanostructures, such as carbon-based nanostructures. The ability of carbon nanostructures to quickly adsorb materials is of benefit to the disclosed devices in certain sensing applications. For example, carbon-based sensing surfaces can be formed from nanotubes, including single-walled nanotubes (SWNT) and multi-walled nanotubes (MWNT), nanobelts, nanorods, nanowires, nanocoils, and the like. Nanostructures of the invention are not limited to carbon-based nanostructures, however, and nanostructures formed of other material can be utilized. For example, nanostructures etched from silicon or including any other suitable conductive (such as Pt or Pd nanoparticles for hydrogen sensing) or semi-conductive material at the surface can be utilized.

III. Detecting the Presence of an Analyte on the Sensing Surface

Figure 3:
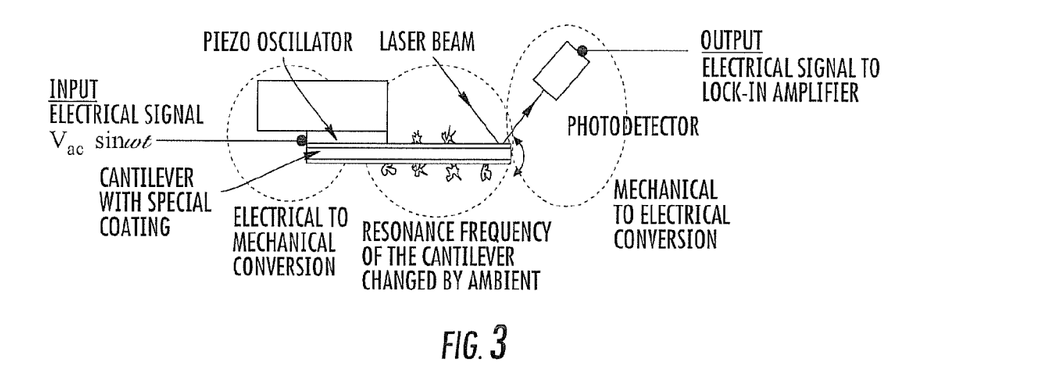
FIG. 3 depicts a schematic diagram of a cantilever resonator based chemical/bio-molecule sensor.

A generic diagram of MEMS/NEMS based sensing is shown in FIG. 3. As can be seen, the electrical signal is converted to mechanical oscillations, which are then converted back to electrical signal to take advantage of high sensitivity and low power requirements of the mechanical resonator. The sensitivity of the cantilever sensor is determined with respect to changes in surface potential and charge. The total force on the cantilever, $F_{tot}$, (which in turn controls the sensitivity) is given by:

$$F_{tot} = \frac{1}{4}\frac{\partial C}{\partial z}V_{ac}^2 + \frac{1}{2}\frac{\partial C}{\partial z}(V_{dc} - V_{con})^2 +$$
$$\left[\frac{\partial C}{\partial z}(V_{dc} - \Delta\phi)\right]V_{ac}\sin(\omega t) - \frac{1}{4}\frac{\partial C}{\partial z}V_{ac}^2\cos(2\omega t)$$
$$= F_{const} + F_\omega + F_{2\omega}$$

wherein C is the tip sample capacitance and $\Delta\phi$ is the difference in work function of the tip and the sample. The different parameters affecting the sensitivity, such as, resonator-reference electrode distance, ac voltage magnitude, area of the resonator, and its quality factor, can be systematically varied.

The sensing technique disclosed herein is based on the change in surface work function of the sensing surface due to adsorption of the target molecules. The present inventors have discovered, through experiments conducted with commercial probes with triangular and rectangular cross-sections and with various stiffness and quality factors, that the surface potential sensitivity of the sensor can be down to one microvolt or less. The sensitivity of the cantilever to surface charge also depends on the factors mentioned herein.

A change in the surface work function of the sensing surface results in the amplitude of resonance (R) of the microcantilever, which can be detected by any detection device or method. For example, the cantilever displacement can be detected, in one particular embodiment, using a laser and photodetector based transduction mechanism. Alternatively, the displacement can be detected using a piezo-resistive cantilever, which will significantly reduce the cost of manufacturing these sensors. The resistance of a piezo-resistive element is proportional to its displacement, which will be used to detect the change in deflection of the cantilever caused by the change in surface potential. In another process, the change in capacitance between the cantilever and the reference electrode, which changes with distance, can be measured to detect the cantilever tip displacement.

The current detection method has the advantage of using a resonating cantilever for detection such that very low surface potential changes and charges can be detected, since the sensitivity of the cantilever resonator depends not only on the Q-factor, but also the cantilever-sample distance (which can be easily controlled), and the area of cantilever (unlike the mass detection where the sensitivity depends only on the Q-factor, or the chem-FET where the current change is fixed depending on the surface potential change). Hence, with the presently disclosed methods, it is possible to approach single molecule detection capability, and easily surpass the detection limit of the other techniques, such as those based on mass changes or surface stress changes, by orders of magnitude. In the present invention, the high sensitivity of the microcantilever resonator sensors with regard to surface potential changes allows the detection device to apply the sensing methodology to detect less than 1000 ppm hydrogen with very low response time, such as about 6 ppm of hydrogen. Likewise, less than 100 ppb of nitrogen, such as about 60 ppb of nitrogen, can be detected.

Thus, surface potential change, caused by adsorbed analyte molecules, can be used as a parameter for sensing chemicals and bio-molecules. The minimum surface potential change as well as the minimum surface charge that is detectable by the displacement of a cantilever sensor is described herein. Sensors based on surface potential change are more sensitive than amperometric methods commonly used, since the signal can be enhanced by optimizing four independent parameters: (1) the distance between the probe and the reference electrode, (2) applying dc voltage simultaneously with the ac voltage $V_{ac}$ to the resonator, (3) the quality factor, and (4) the area of the probe. The charge is affected by the first three parameters.

Figure 4:
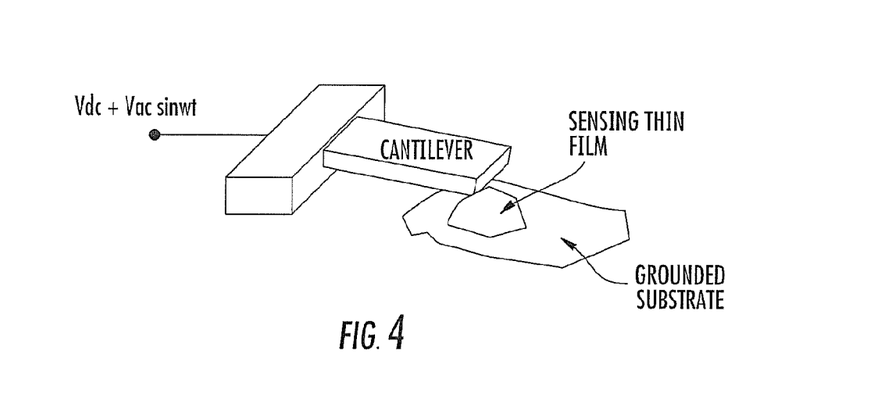
FIG. 4 depicts an exemplary setup for a gas sensing detection system.

FIG. 4 shows an exemplary sensing experiment. The cantilever displacement in that setup is detected using a laser. In an alternative embodiment, displacement can be detected using a piezoelectric or piezoresistive cantilever. The ac current flowing through a piezoelectric element is proportional to its displacement. The SILAR (Successive Ionic Layer Adsorption and Reaction) process involving $Pb(OAc)_2 3H_2O$, $Zr(O''Pr)_4OH$ and $Ti(O''Bu)_4$ solutions can be used to create PZT films on the cantilevers in a cheap and industrially relevant process. This will reduce the costs of manufacturing suck sensors considerably.

Figure 7:
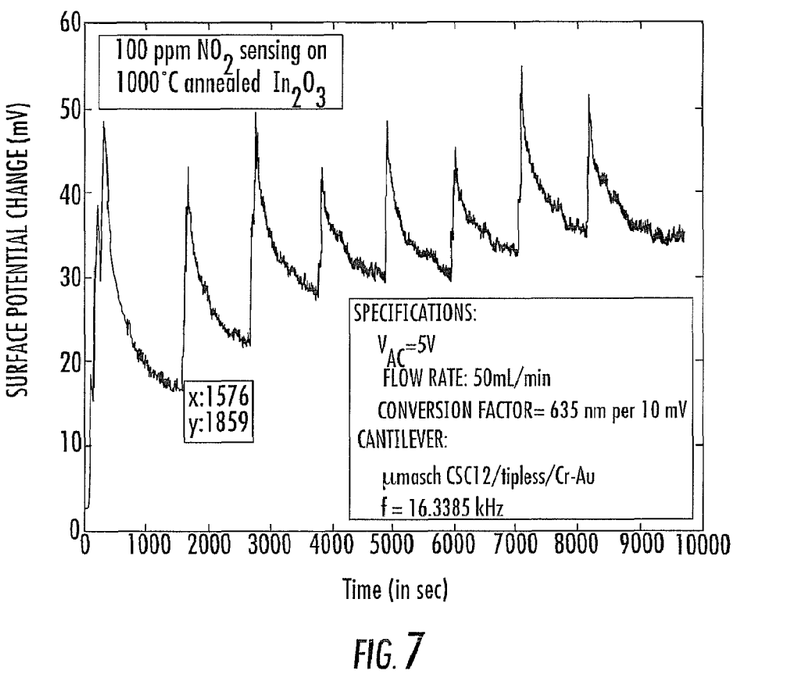
FIG. 7 shows $NO_2$ sensing using an $In_2O_3$ film annealed in 1000° C. in air.

Once the surface potential changes of different analyte molecules on specific functionalized materials have been characterized, the presence of gases in mixtures can be determined. It is rare that a perfect functionalizing material can be found for a particular type of analyte molecule, which will not have any interference from other molecules ("specificity"). To circumvent this problem, an n-dimensional signature of a particular type of analyte molecule can be determined with respect to the surface potential changes in an array of n different functionalized electrodes as shown in FIG. 7. Several electrodes, containing special coating (such as CNT, Au, or transition metal oxides such as $In_2O_3$, $WO_3$, $SnO_2$) for selectively interacting with specific molecules in air or liquid, can be fabricated on an insulating substrate (called a sensor cassette). The sensor cassette can be moved in x and y directions, so that a particular electrode can be positioned under the fixed cantilever (oscillating in the z-direction). The incoming molecules will interact with the specific electrodes, and produce changes in chemical potential, which will be measured by the cantilever, and subsequent circuitry. Once the signatures of the individual analyte molecules have been determined, the presence of different analyte molecules in a gas mixture can be sensed by using a computer, which can be interfaced with the sensor to obtain the n-dimensional data for a given gas mixture, and which can be compared against a database containing the signatures for a spectrum of target analyte molecules. Again the displacements of the individual cantilevers can be determined by measuring the ac current of a piezoelectric or piexoresistive film deposited on the cantilevers.

EXAMPLES

The following examples illustrate the development of sensors using chemical deposition as disclosed herein and is not meant to limit the scope of the invention:

Example 1

The magnitude of the coulombic force of attraction is orders of magnitude higher (for small distances) than any other force. Thus, it is possible to detect a single ionized molecule based on its charge, rather than its mass or any other effects on the surface (such as induced stress or even change in surface potential).

Detailed measurements have been carried out to demonstrate the sensitivity of the proposed technique as well as to understand the interaction between the chemical/bio-molecules and the substrates coated with functionalized thin films. For testing bio-molecules in fluid media, a special fluid cell can be used. The cell can be modified slightly (replacing the O-ring and the rubber base with inert materials) so that toxic chemical molecules in gaseous form, such as NOx, $NH_3$, $H_2S$, and hydrogen (due to its combustible properties) can be tested.

For chemical sensing, the initial focus was on studying the interaction between hydrogen and nitrogen oxides with Palladium and Platinum coated substrates. Hydrogen detection using Pd (or Pt)/SiC schottky diodes has been performed, and it is believed that the adsorption of the gaseous species in the metal increases the schottky barrier height reducing the schottky diode current. It has been shown that nitrogen oxides (and even hydrocarbons) also have the capability to alter schottky barrier heights, especially when the schottky metal is platinum. The sensitivity, temporal response, and selectivity of gas sensing using both Pd and Pt coated metal substrates has been studied.

The effect of reducing gases on the transition metal oxides is demonstrated herein. Gases such as NOx, $NH_3$, $H_2S$ have the property of releasing or accepting electrons when in contact with transition metals such as $In_2O_3$, $SnO_2$ and ZnO. The reference electrodes are coated with these materials and the surface potential changes are measured at room temperature and at elevated temperatures.

Disclosed herein is an $NO_2$ sensor developed using the above outlined principles by coating $In_2O_3$, $SnO_2$ and mixtures of $In_2O_3$ and $SnO_2$ onto a ground substrate coated with a functionalized film. The process used to create these films is not the more commonly used physical deposition using sputtering or pulsed laser deposition but an economically attractive chemical deposition technique (SILAR), which lends itself to commercialization.

Example 2

Figure 10:
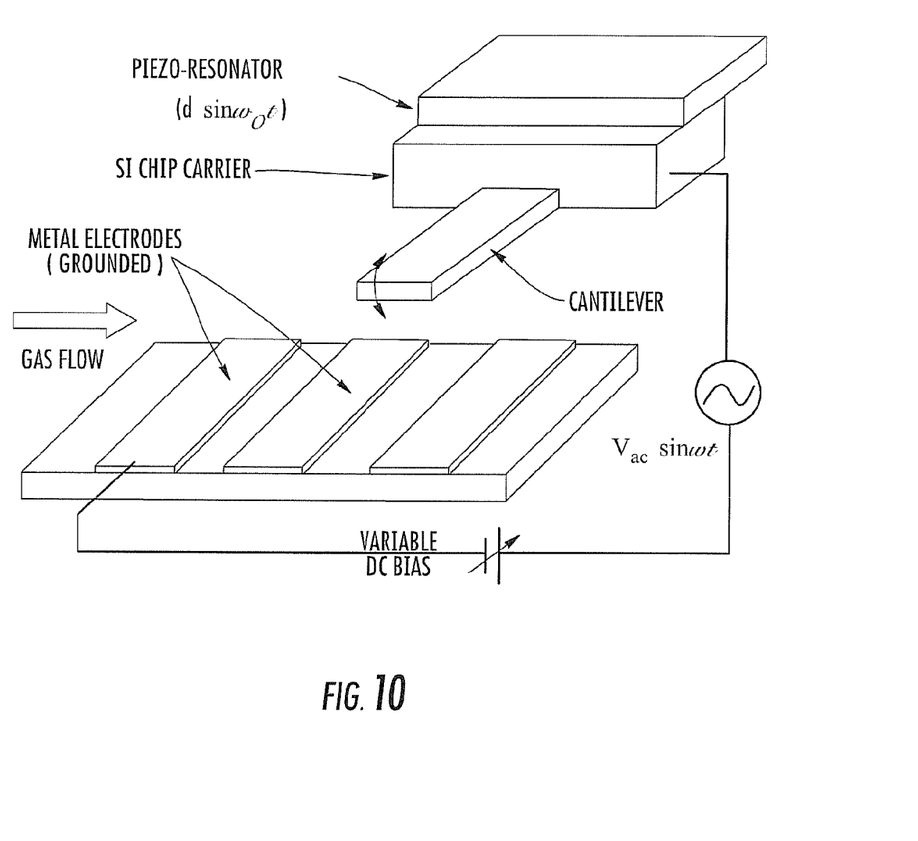
FIG. 10 shows a schematic diagram of the measurement set up. The cantilever has only a small overlap with the stripe metal electrode to minimize parasitic capacitances. The cantilever is excited by the piezo at a frequency $\omega_0$, and by the applied biases at a frequency $\omega$, slightly different from $\omega_0$.

The following experiment illustrates the high sensitivity of microcantilever resonator sensors with regard to surface potential change:

Measurements were carried out with uncoated Si cantilevers, as well as ones coated with 10-15 nm Pt, using a commercial atomic force microscope (AFM) set up. The resonance frequencies of the cantilevers were ~20 KHz, and the spring constant ~0.08 N/m. To achieve high sensitivity, the cantilevers were made to oscillate at a frequency $\omega$, very close to the resonance frequency $\omega_0$, using an ac (frequency $\omega_0$) and a dc bias applied to the cantilever. The amplitude of oscillations of the cantilever was detected by creation of amplitude modulation of the cantilever (through formation of beats) by simultaneous application of another periodic excitation using the piezo resonator of the AFM at frequency $\omega_0$ (see FIG. 10). The beat frequency $\omega-\omega_0$ was kept low (~2.5 Hz) so that the AFM feedback module can easily respond to it, and move the cantilever accordingly. Since this would be difficult to detect otherwise, the change in oscillation amplitude was detected by the AFM feedback mechanism, which moves the piezo-positioner up and down in response to changes in amplitude of the oscillations. For the highest sensitivity, the cantilever was positioned above a striped Au pattern (reference electrode biased to ground) with small overlap (~30 µm) between the cantilever and the reference electrode (see FIG. 10). This ensured that the parasitic capacitance associated with the cantilever assembly remained low.

Figure 11:
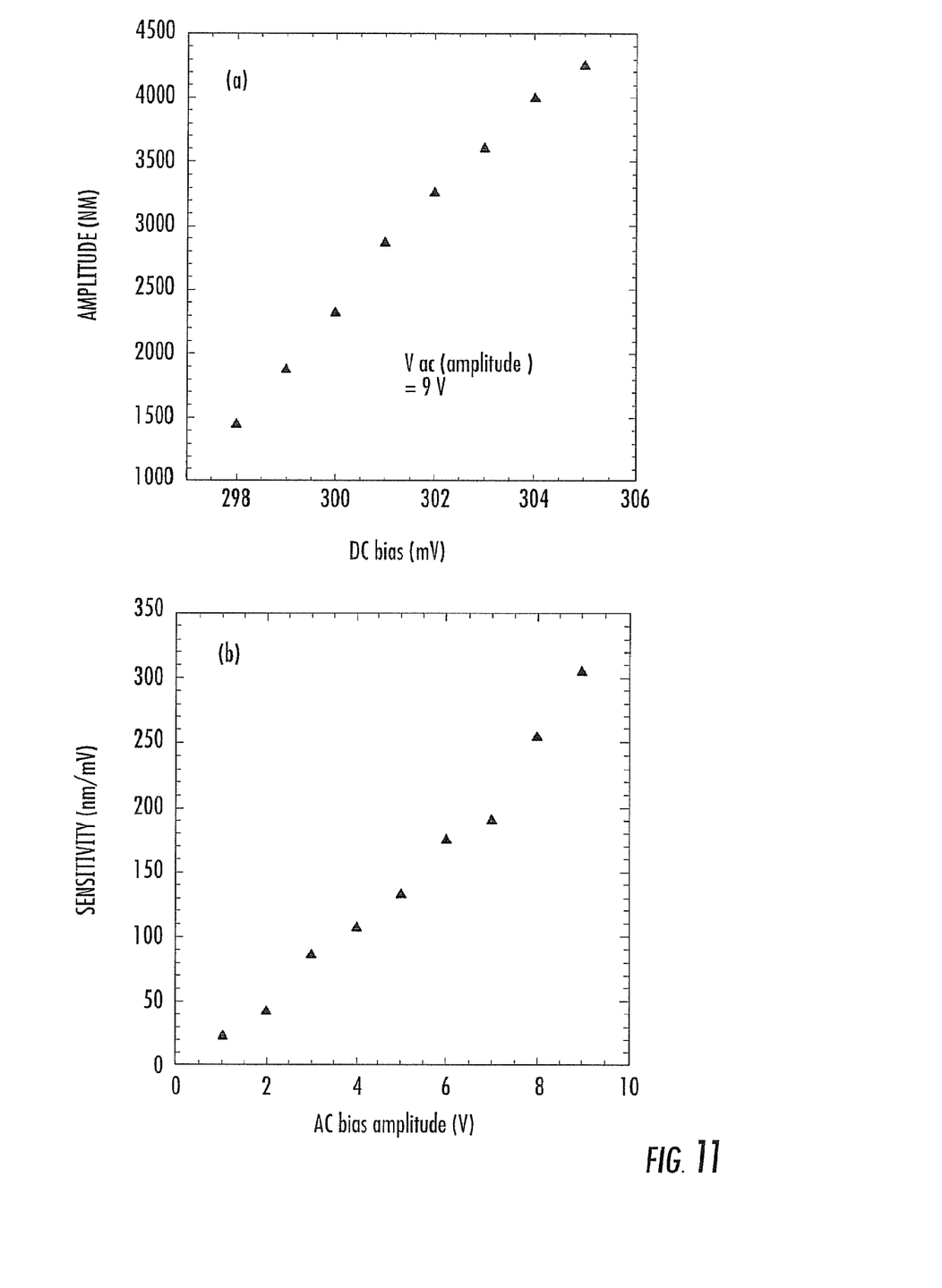
FIG. 11 shows (a) variation of the beat oscillation amplitude of the cantilever as a function of dc bias (note that this amplitude corresponds to the actual slow movement of the piezo-resonator and hence of the cantilever, which is caused by the feedback mechanism to maintain a constant amplitude of oscillation) and (b) variation of the oscillation amplitude as a function of ac bias. The sensitivity is calculated as the ratio of the change in oscillation amplitude to a change in dc bias.

The ω-component of the total electrostatic force $F_\omega$, acting on the cantilever under an applied ac bias $V_{ac} \sin \omega t$, and a dc bias $V_{dc}$, is given as $$F_\omega = \frac{\partial C}{\partial z}(V_{dc} - \Delta\phi)V_{ac}\sin\omega t, \text{ where } \frac{\partial C}{\partial z}$$

is the capacitance gradient of the cantilever, and $\Delta\phi$ is the difference in work function of the cantilever and the gold reference electrode. Under resonant oscillations, the oscillation amplitude for the cantilever will be $QF_\omega/k$, where k is the spring constant of the cantilever. We first determined the dc and ac sensitivity, and the noise floor of the cantilever sensor. The sensitivity data for uncoated Si cantilevers is shown in FIG. 11. The amplitude of beat oscillations is plotted against dc bias in FIG. 11a (for a constant ac bias of 9 V amplitude), which shows the sensitivity to be ~400 nm/mV. The variation of sensitivity with ac bias is plotted in FIG. 11b, and we can see that the sensitivity increases almost linearly with increase in ac bias, and reaches a value ~306 nm/mV, for an ac bias of amplitude 9V. The tip-sample distance for these measurements was determined to be >10 µm. The rms noise for these measurements was determined from a scan taken with constant dc and ac biases, to be ~20 nm. The high noise is due to the high AFM feedback gain used, the noise in the biases, and thermal noise. Nevertheless, the minimum dc bias change that can be sensed using this setup for a 9V ac bias applied is found to be about 50 µV. This can be easily improved by reducing the cantilever-sample distance, as well as increasing the ac bias. Increasing the cantilever area and Q-factor, and reducing the spring constant, will also proportionally increase the sensitivity. The sensitivity of normal Kelvin probe microscopy where the cantilever is excited (with the ac bias) far from the resonance frequency is usually a few mV. The sensitivity enhancement by a factor of ~50 is almost entirely due to the quality factor enhancement [in our study, $Q=\omega_0/2\Delta\omega=19200/(2\times200)=48$; $\Delta\omega$=bandwidth]. We have not presented the sensitivity enhancement data for lower distances, because in the current setup the magnitude of the beat oscillations does not increase significantly with distance. This is because, although the capacitive force $F_\omega$ increases sharply with distance, the magnitude of non-contact mode oscillations decreases quickly with distance, compensating any increase in the beat amplitude. However, we have measured the amplitude of the capacitive force $F_\omega$, using a spectrum analyzer, and that increases with distance following a square law, as expected.

From the data for overall cantilever capacitance and the minimum detectable surface potential $\Delta V$, the minimum detectable charge $\Delta Q$ can be calculated. Assuming that about 30 µm of the cantilever (with width ~35 µm) overlaps with the metal electrode, and the cantilever-electrode distance is ~10 µm, the effective capacitance is ~1 fF (parallel plate approximation). From $\Delta V=50$ µV, $\Delta Q=C\Delta V=0.31$ q, where q is the electronic charge. If there were only the effective capacitance (and no parasitic capacitance) between the cantilever edge and the metal electrode, then we could have seen step rise in the beat amplitude with dc bias applied to the tip could be seen. But the much higher parasitic capacitance (on the order of pF) is probably masking such effects. Nevertheless, since the force is only dependent on the cantilever-electrode capacitance, it can be concluded that single electronic charge (such as from ions hitting the cantilever) should be possible to detect using this technique.

Figure 12:
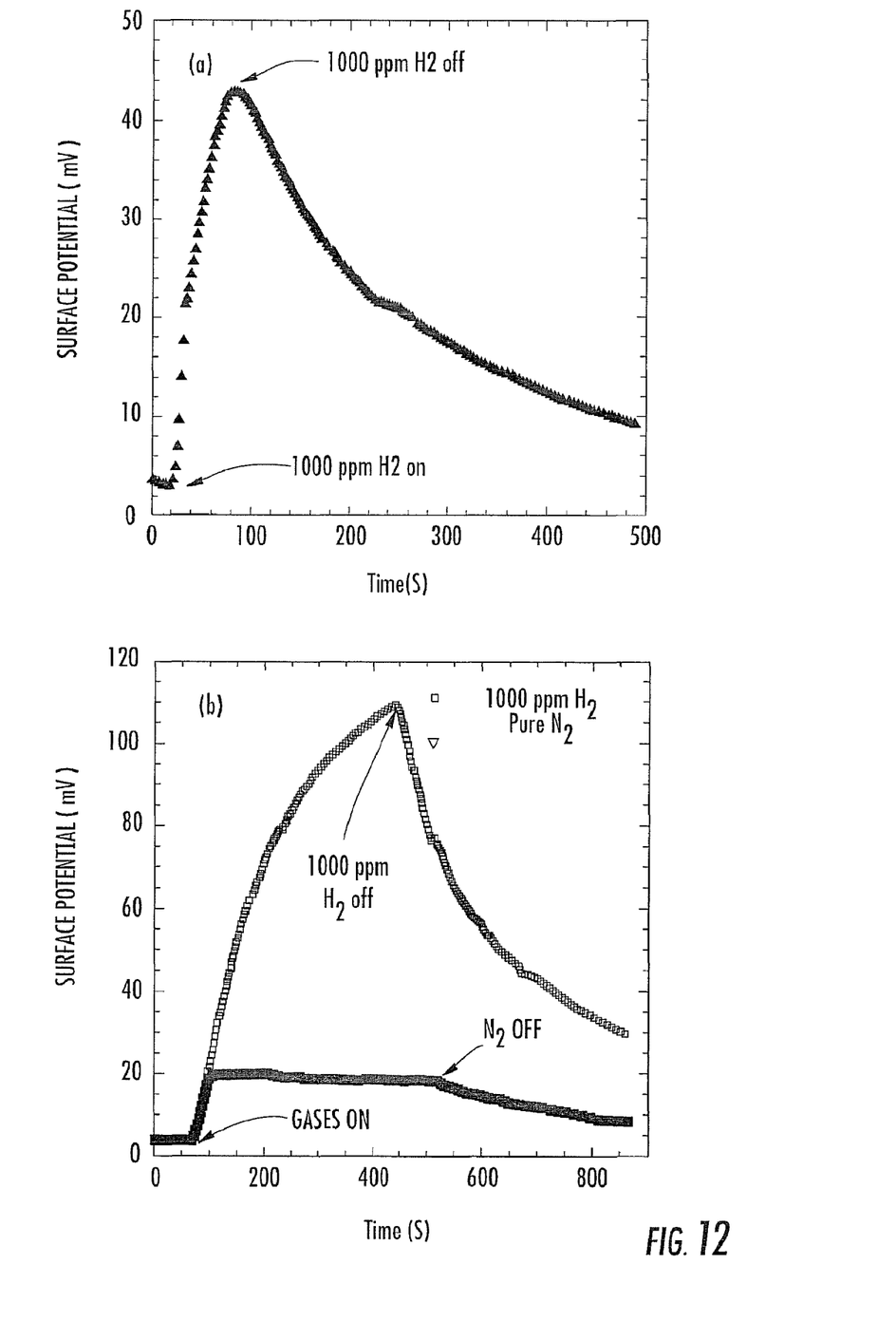
FIG. 12 shows (a) surface potential rise and fall transients as the 1000 ppm hydrogen is switched on and off and (b) comparison of the surface potential transients for 1000 ppm hydrogen and pure nitrogen, as they are switched on and off.

To exploit the sensitivity of this technique for practical applications, the cantilever sensor was used to detect 1000 ppm hydrogen by coating the cantilever with platinum. Platinum was chosen since it has the unique property of adsorbing hydrogen. However, the mechanism of hydrogen's interaction with platinum, especially in terms of work function change under ambient conditions, is not well understood. Very few studies have been reported, and mostly under high vacuum conditions. It is contended from these studies that the change in work function (magnitude and sign) depends on the surface coverage of hydrogen on the platinum surface. Although not the major focus in this study, the cantilever based potentiometric sensor described here can serve as a very sensitive measurement tool (much more sensitive than conventional Kelvin probe, due to Q-factor enhancement as discussed earlier) for changes in surface potential due to adsorbed or attached molecules on exposed surfaces. The change in surface potential when 1000 ppm hydrogen (balance nitrogen) is flown over the Pt coated cantilever is shown in FIG. 12a. The surface potential change was calculated as the ratio of the change in oscillation amplitude (nm) and sensitivity (nm/mV). Since the maximum oscillation amplitude possible is only 4 µm in the current system, the applied dc bias was changed manually to reset the amplitude to a predetermined low value, each time the 4 µm amplitude was reached. Thus several segments of the data have to be put together, which explains the slight non-uniformity in the overall response curve. Nevertheless, we do see a large change in surface potential of ~40 mV, from the point the 1000 ppm hydrogen is switched on, to the point when it is switched off. From the minimum detectable potential change of ~0.05 mV, and a rise rate of 0.7 mV/s (computed between 20 mV and 30 mV for reasons discussed below), the lower limit of the detection time is estimated to be ~70 ms, which is quite remarkable considering the fact that there is a lot of room for improvement in sensitivity. The fall in surface potential is slower compared to the rise, which could be caused in part by the delay in getting the hydrogen out of the inlet pipe by the purge nitrogen gas. To safeguard against any artifacts, we compared the effects of flowing pure $N_2$ gas and 1000 ppm hydrogen, and the result is shown in FIG. 12b. We find that the cantilever oscillation magnitude increases (as shown by a change in equivalent surface potential) initially from the equilibrium condition, even when pure nitrogen is flown. However, the surface potential quickly reaches a steady state value of ~20 mV (for this reason, the rise rate above is calculated after 20 mV) after which the potential does not rise even though the flow is continued. On the other hand, when hydrogen is flown continuously, the surface potential initially rises sharply, just like the nitrogen flow, and then continues to rise at a rate that becomes slower with time, until the flow is switched off. We conclude that the surface coverage of the hydrogen molecules increases with time, monotonically changing the surface potential. The initial increase in oscillation amplitude is likely caused by the flow of gas under the cantilever, which drags the cantilever toward the surface due to reduced pressure (from Bernoulli's principle) and that increases the electrostatic force. The resonant frequency of the cantilever did not change during the hydrogen adsorption, since the beat frequencies were found to remain constant. This was also verified using a spectrum analyzer. Therefore, it rules out any contribution from the surface stress change to the measured amplitude data (through changes in resonance frequency).

Example 3

The following experiment illustrates the development of sensors using chemical deposition as disclosed herein:

The sensing thin films of $In_2O_3$ and $SnO_2$ on Si substrates were prepared using aqueous solutions of $In(NO_3)_3xH_2O$, $InCl_3xH_2O$, $SnCl_2xH_2O$, and NaOH. The Si substrates were previously fired in a furnace at 1000° C. for 30 min. The $In_2O_3$ and $SnO_2$ were fabricated by SILAR (Successive Ionic Layer Adsorption and Reaction) and SDH (Successive Dipping Heating) deposition methods. The substrate was attached to the arm of a Gilson 223 XYZ robotic sample changer. Using the SILAR method the dipping sequence in an In-containing solution, water, an NaOH solution, and water was 3 seconds, 6 seconds, 3 seconds, 6 seconds and in a Sn-containing solution, ethanol, water, ethanol, it was 3 seconds, 6 seconds, 3 seconds, 6 seconds established to obtain $In_2O_3$ and SnO2 films respectively. Using the SDH method, the substrate was successively immersed in In or Sn-containing alcohol solutions and a heating zone (about 50° C.) for 1 second and 20 seconds for $In_2O_3$ or 10 seconds for $SnO_2$. The procedures of dipping and heating were performed at the speed of about 1 mm/second. The coated films were directly annealed in air at 600, 800, 1000, or 1100° C. in a preheated box furnace.

Figure 5:
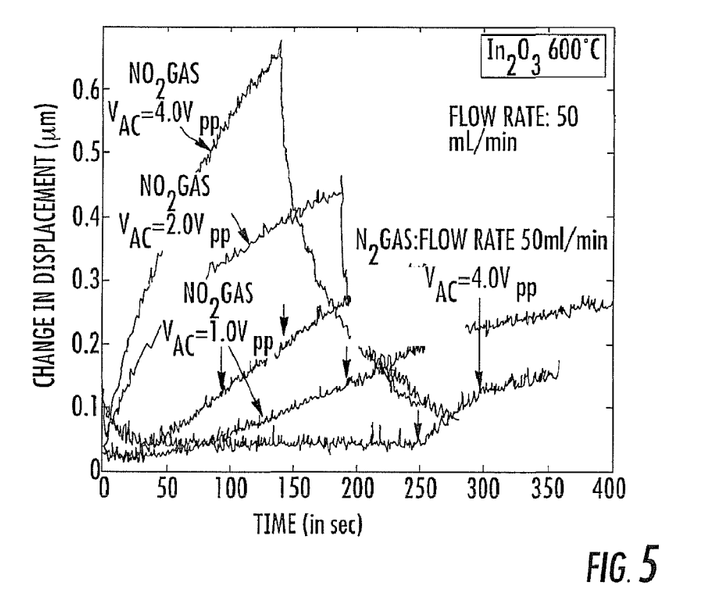
FIG. 5 shows $NO_2$ sensing using an $In_2O_3$ film annealed in 600° C. in air.

FIG. 5 reveals that with $In_2O_3$ films made in the above mentioned process and annealed in air at about 600° C., $NO_2$ can be detected and that the signal can be enhanced by increasing $V_{ac}$. The $NO_2$ was diluted with Ar to a concentration of 100 ppm for these experiments.

Figure 6:
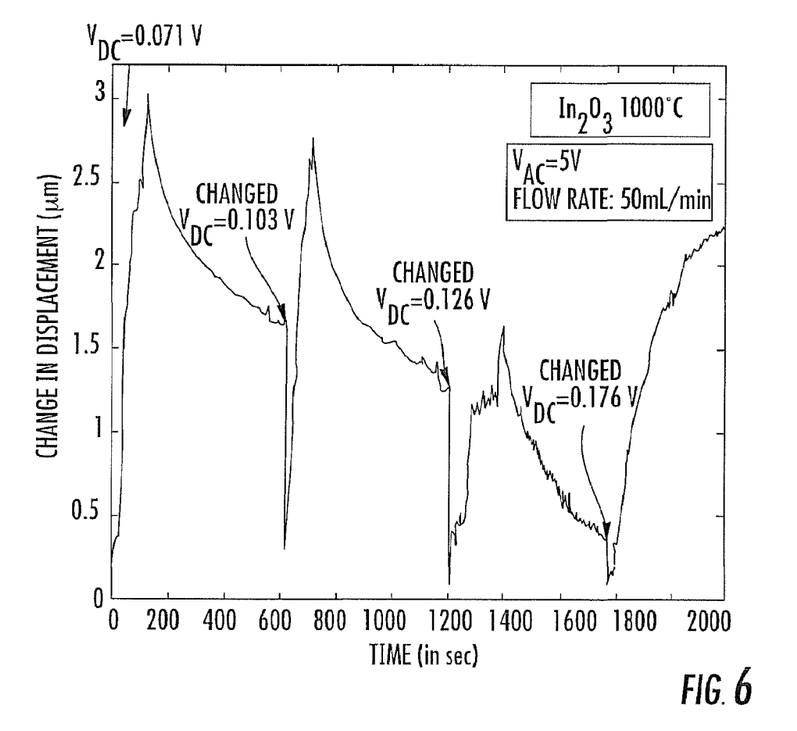
FIG. 6 shows $NO_2$ sensing using an $In_2O_3$ film annealed in 1000° C. in air.

However, as shown in FIG. 6, annealing the SILAR film at about 1000° C. in air results in an $In_2O_3$ film that allows the detection of $NO_2$ at a faster rate and at much lower concentrations, as evidenced by the larger change in cantilever displacement. The other experimental conditions used were a gas containing 100 ppm of $NO_2$ and a flow rate of 50 ml/minute.

The response time of the sensor can be reduced to a few seconds after optimization as shown in FIG. 7, where the actual surface potential variation in response to $NO_2$ is measured. The experimental conditions used were 100 ppm $NO_2$ on $In_2O_3$ annealed in a 1000° C. in air at a flow rate of 50 ml/minute and Vac=5V.

Figure 8:
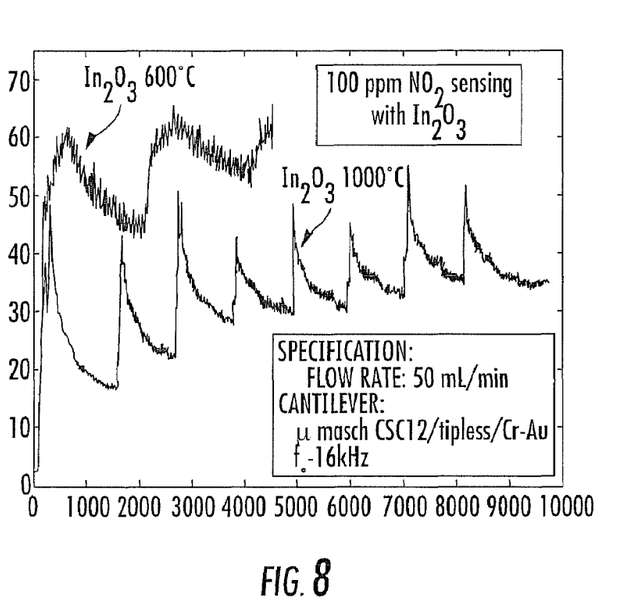
FIG. 8 shows $NO_2$ sensing comparing $In_2O_3$ films annealed in 600° C. and 1000° C. in air.
Figure 9:
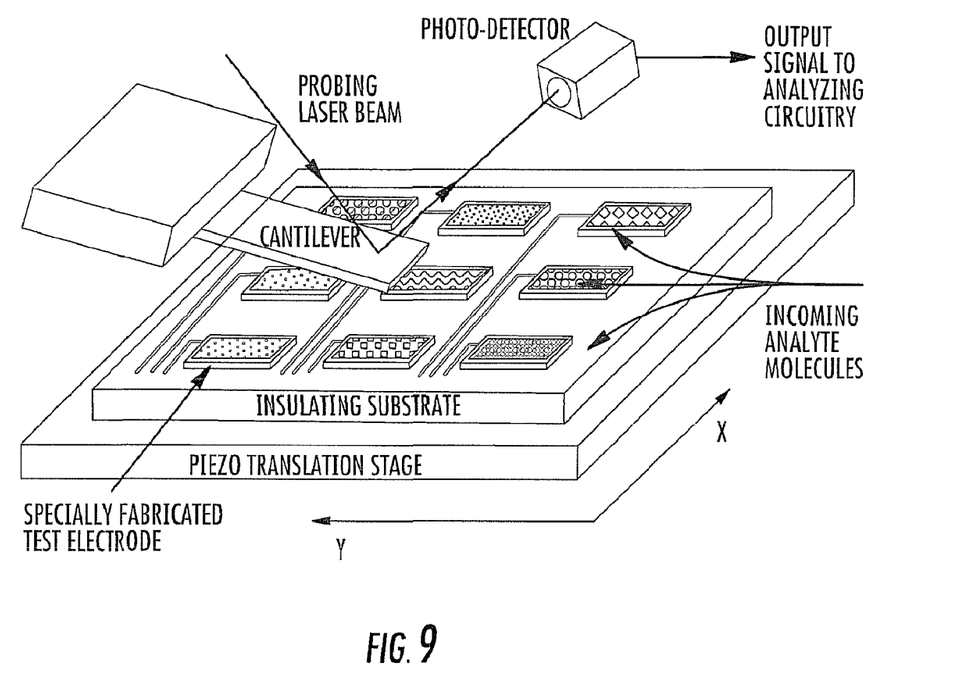
FIG. 9 shows a conceptual diagram of the chemical and bio-molecule sensor with individually addressable test (analyte) electrodes where the Translation Stage can move the substrate in x and y directions to bring the desired electrodes under the cantilever for sensing.

In FIG. 8, a direct comparison of two $In_2O_3$ films is shown, one annealed at 600° C. and the other at 1000° C. This comparison reveals the superiority of the higher annealing temperature for sensing applications.

Example 4

Graphene

The graphene films are made through mechanical exfoliation of graphite (from, for example, either a pencil or a piece of carbon) onto a rough substrate.

Figure 13:
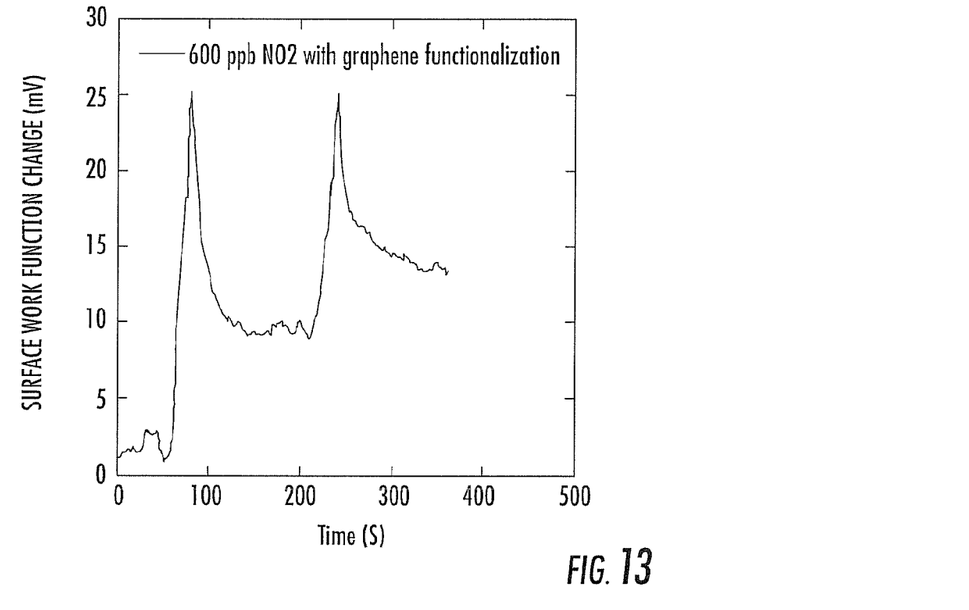
FIG. 13 shows a comparison of 600 ppb $NO_2$ sensing using graphene layer produced by abrasion of pencil graphite.

FIG. 13 shows the fast rise and fall time of the surface work function which is registered when exposed to $NO_2$. The fall-off indicates that the surface saturates after multiple exposures. However, the graphene surface can be reactivated using nitrogen as a flush gas. The detection levels realized allow us to extend this type of $NO_2$ sensor into the low part-per-billion range.

This invention presents the opportunity to develop very inexpensive sensors, e.g. $NO_2$ sensors, in the part-per-billion range where the graphene sensing surface can be discharged after a measurement due to its low cost. This would prevent the long time degradation of such a surface due to humidity and exposure to other gases and provide a clean and activated surface at the beginning of each measurement.

Figure 14:
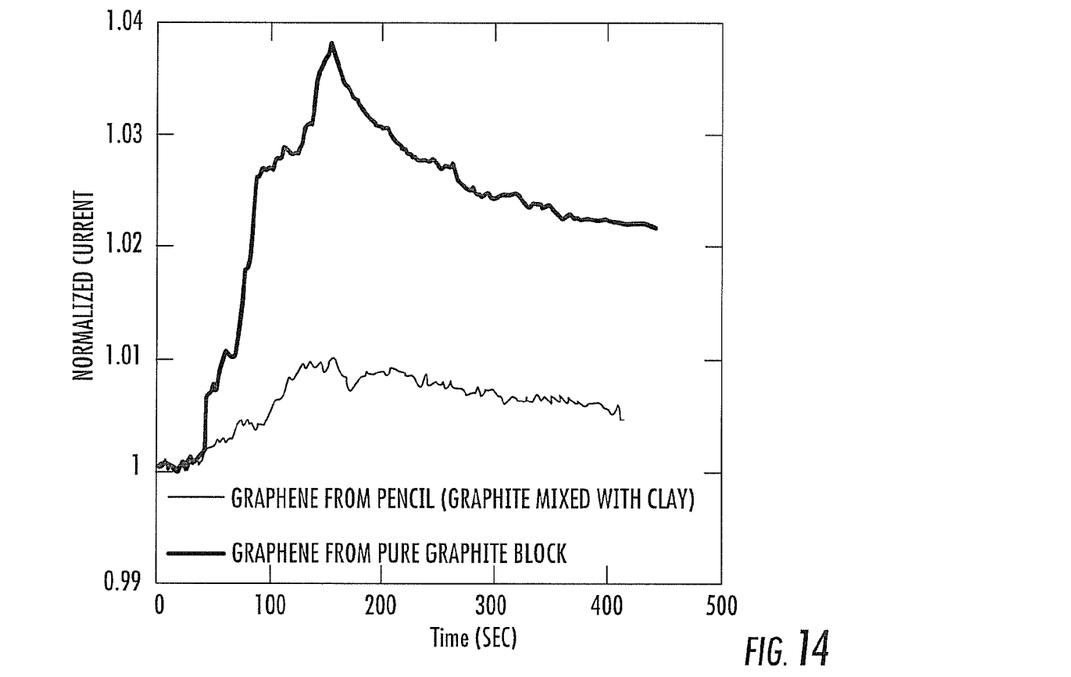
FIG. 14 shows a comparison of the change in current flow between two contacts established on the sensing films (a) graphene produced by abrasion of pure graphite, and (b) graphene produced by abrasion of pencil graphite, as 8 ppm $NO_2$ flow is switched ON and OFF.

In addition to pencil lead being used as the source of graphite, pure graphite has also been studied. Initial conduction based measurements suggest that graphene layers obtained from pure graphite may be even more sensitive than that obtained from the pencil graphite, which is also mixed with clay. The comparison of the change in current flow through the contacts is shown in FIG. 14.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

The invention claimed is:

1. A system for detecting the presence of an analyte, the system comprising:
   a non-contact microcantilever device comprising a resonating element, wherein the resonating element does not bond to the analyte;
   a counter electrode positioned within working proximity from the resonating element, the counter electrode comprising a sensing surface configured to bond to the analyte; and
   a detection device configured to monitor the movement of the resonating element.

2. A system as in claim 1, wherein the non-contact microcantilever device is positioned within a vacuum.

3. A system as in claim 1, wherein the sensing surface comprises a layer of graphite.

4. A system as in claim 1, wherein the sensing surface comprises a nanostructure.

5. A system as in claim 4, wherein the nanostructure comprises a carbon nanostructure.

6. A system as in claim 1, wherein the detection device comprises a laser and photodetector based transduction mechanism.

7. A system as in claim 1, wherein the non-contact microcantilever device comprises a piezo-resistive cantilever, and wherein the detection device measures the resistance of the piezo-resistive cantilever to detect the change in deflection of the resonating element caused by a change in surface potential.

8. A system as in claim 1, wherein the sensing surface comprises a plurality of different functionalized electrodes.

9. A system as in claim 8, wherein the non-contact microcantilever device is configured to move across the sensing surface in a plane that is parallel with the sensing surface such that the resonating element can be positioned in working proximity to each of the differently functionalized electrodes.

10. A method of forming a detection system for detecting the presence of an analyte, the method comprising:
    providing a non-contact microcantilever device comprising a resonating element, wherein the resonating element does not bond to the analyte;
    forming a sensing surface on a counter electrode, wherein the sensing surface is configured to bond to the analyte;
    positioning the microcantilever device and the sensing surface on the counter electrode within working proximity; and
    providing a detection device configured to monitor the movement of the resonating element.

11. A method as in claim 10, wherein the non-contact microcantilever device is positioned within a vacuum.

12. A method as in claim 10, wherein the sensing surface comprises a layer of graphite.

13. A method as in claim 10, wherein the detection device comprises a laser and photodetector based transduction mechanism.

14. A method as in claim 10, wherein the non-contact microcantilever device comprises a piezo-resistive cantilever, and wherein the detection device measures the resistance of the piezo-resistive cantilever to detect the change in deflection of the resonating element caused by a change in surface potential.

15. A method as in claim 10, wherein the sensing surface comprises a plurality of different functionalized electrodes.

16. A method as in claim 15, wherein the non-contact microcantilever device is configured to move across the sensing surface in a plane that is parallel with the sensing surface such that the resonating element can be positioned in working proximity to each of the differently functionalized electrodes.

17. A method of detecting the presence of an analyte, the method comprising:
   providing a detection system comprising a non-contact microcantilever device positioned within working proximity to a counter electrode, wherein the microcantilever device comprises a resonating element that does not bond to the analyte, and wherein the counter electrode comprises a sensing surface configured to bond to an analyte; and
   detecting the change in surface work function or charge configurations of the sensing surface utilizing a detection device configured to monitor the movement of the resonating element.

18. A method as in claim 17, wherein the non-contact microcantilever device comprises a piezo-resistive cantilever, and wherein the detection device measures the resistance of the piezo-resistive cantilever to detect the change in deflection of the resonating element caused by a change in surface potential.

19. A method as in claim 17, wherein the sensing surface comprises graphite.

20. A method as in claim 17, wherein the sensing surface comprises a plurality of different functionalized electrodes, and wherein the non-contact microcantilever device is configured to move across the sensing surface in a plane that is parallel with the sensing surface such that the resonating element can be positioned in working proximity to each of the differently functionalized electrodes.

* * * * *